United States Patent [19]
Umezawa et al.

[11] 3,988,315
[45] Oct. 26, 1976

[54] ANTIBIOTICS ACLACINOMYCINS A AND B

[75] Inventors: Hamao Umezawa, Tokyo; Tomio Takeuchi, Tokyo; Masa Hamada, Hoya; Akira Takamatsu, Yokohama; Toshikazu Oki, Kamakura, all of Japan

[73] Assignee: Zaidan Hojin Biseibutsu Kagaku Kenkyu Kai, Tokyo, Japan

[22] Filed: July 16, 1975

[21] Appl. No.: 596,682

[30] Foreign Application Priority Data
July 27, 1974 Japan.............................. 49-86390

[52] U.S. Cl................................ 536/17; 195/80 R; 424/181; 536/4
[51] Int. Cl.²......................................... C07H 17/08
[58] Field of Search................... 260/210 AB, 210 R

[56] References Cited
OTHER PUBLICATIONS

Gottlieb et al., "Antibiotics", vol. I, Springer-Verlag, New York, 1967, pp. 190–204.
Berg, et al. "Chem. Abst." vol. 73, 1970, pp. 54,265r.
Keller–Schierlein et al. "Antimicrobial Agents and Chemotherapy", 1970, pp 68–74.

*Primary Examiner*—Johnnie R. Brown
*Attorney, Agent, or Firm*—Herbert W. Taylor, Jr.

[57] ABSTRACT

New antitumor agents named aclacinomycins A and B, which are anthracycline glycosides and inhibit the growth of various microorganisms e.g., *Staphylococcus aureus, Micrococcus flavus, Corynebacterium bovis* and inhibit the growth of animal tumors such as leukemia L1210 and P388 and lymphoma 6C3HED in mice and hepatomas in rats are produced by the fermentation of a microorganism belonging to the genus Streptomyces which has been designated *Streptomyces galilaeus* (MA144–M1 and A.T.C.C. 31133); they are recovered from the broth by conventional methods for recovering antibiotics.

3 Claims, 6 Drawing Figures

ULTRAVIOLET AND VISIBLE ABSORPTION SPECTRA OF ACLACINOMYCIN A

FIG. 2 INFRARED ABSORPTION SPECTRUM OF ACLACINOMYCIN A IN KBr

NMR SPECTRUM OF ACLACINOMYCIN A (100 MHz IN CDCl₃, INTERNAL REFERENCE: TMS)

ULTRAVIOLET AND VISIBLE ABSORPTION SPECTRA OF ACLACINOMYCIN B

FIG. 5 INFRARED ABSORPTION SPECTRUM OF ACLACINOMYCIN B IN KBr

NMR SPECTRUM OF ACLACINOMYCIN B (100 MHz IN CDCl₃, INTERNAL REFERENCE: TMS)

ANTIBIOTICS ACLACINOMYCINS A AND B

BACKGROUND OF THE INVENTION

1. Field of the Invention

This invention relates to new anthracycline glycoside antitumor antibiotics and to their production. More particularly, it relates to new antitumor antibiotic substances designated aclacinomycins A and B and to processes for the preparation thereof by the fermentation of a strain Streptomyces galilaeus (e.g., MA144-M1), to methods for their recovery and purification, and to their application as cancer chemotherapeutic agents.

2. Description of the Prior Art

A number of anthracycline glycosides have been found in the cultured broth of Streptomyces. Among them, daunomycin and adriamycin are particularly being watched with keen interest in the field of cancer chemotherapy and have already been applied clinically for human cancers. In the continuation of the study of antitumor antibiotics, the present inventors discovered new compounds and after characterization and purification based on their physico-chemical properties, they confirmed that these antibiotics now named aclacinomycin A and B are new compounds which show low cardiotoxicity and potent antitumor activity in various animal tumors, and they established processes and methods for their production and isolation.

Farmitalia's U.S. patent on adriamycin (B-106FI; 14-hydroxy-daunomycin; INN is Doxorubicin) is U.S. Pat. No. 3,590,028 claiming the product by structure and disclosing its direct fermentation by S. peuceticus var. caesius. Farmitalia also issued U.S. Pat. No. 3,803,124 on chemical conversion of daunomycin to adriamycin; for direct fermentation of daunomycin (as antibiotic FI 1762) by S. peuceticus see U.K. Pat. No. 1,003,383.

Farmitalia's daunomycin (U.S. Pat. No. 1,003,383) may be the same as Rhone-Poulenc's 13057 R.P. (formerly rubidomycin and now Daunoribicin (U.K. Pat. Nos. 985,598; 1,188,262; 1,241,750 and see U.S. Pat. No. 3,616,242) and is "probably" identical with Ciba's danubomycin (U.S. Pat. No. 3,092,550; U.K. Pat. No. 901,830). See also U.S. Pat. No. 3,686,163 on dihydrodaunomycin.

Cinerubin A and cinerubin B are disclosed in U.K. Pat. No. 846,130 and see also U.S. Pat. No. 3,864,480 and Keller-Schierlein et al., Antimicrobial Agents and Chemotherapy, page 68 (1970) and Chemical Abstracts, 54, 1466i (1960).

For further illustrative and summary disclosures of anthracycline antibiotics see Index of Antibiotics from Actinomycetes, Hamao Umezawa, Editor-in-chief, University Park Press, State College, Pennsylvania, U.S.A. (1967) as follows:

| Antibiotic | Page Number |
|---|---|
| Aklavin | 111 |
| Cinerubin A | 220 |
| Cinerubin B | 221 |
| Danubomycin | 242 |
| Daunomycin | 243 |
| Pyrromycin | 542 |
| Rhodomycin A,B | 561 |
| Rubidomycin | 574 |

The textbook Antibiotics, Volume 1, Mechanism of Action, edited by David Gottlieb and Paul D. Shaw, Springer-Verlag New York, Inc., N.Y., N.Y. (1967) at pages 190-210 contains a review by A. DiMarco entitled Daunomycin and Related Antibiotics.

Information Bulletin, No. 10, International Center of Information of Antibiotics, in collaboration with WHO, December, 1972, Belgium, reviews anthracyclines and their derivatives For a description of Streptomyces galilaeus see Arch. fur Mikrobiol., 31, 356 (1958) and International Journal of Systematic Bacteriology, 22, 298 (1972).

This specification on page 37 refers to disclosures by K. Eckardt et al. on galirubins; see Chemical Abstracts 64, 3896g and 67, 90573z.

SUMMARY OF THE INVENTION

There are provided by the present invention the antitumor agents aclacinomycins A and B. These substances are produced by cultivating an aclacinomycin-producing strain of Streptomyces galilaeus in an aqueous carbohydrate solution containing organic nitrogenous nutrients under submerged aerobic conditions until a substantial quantity of aclacinomycin A and B is formed in said solution. Aclacinomycin A and B in cultured broths thus produced can be extracted and purified by conventional methods used for extraction and purification of water-insoluble antibiotics. This invention also embraces aclacinomycins A and B as crude solids, as purified solids, as their salts and as DNA-complexes.

There is thus provided by the present invention the antitumor antibiotic aclacinomycin A which a. is effective in inhibiting the growth of ascites and solid forms of Ehrlich carcinoma, Sarcoma 180, lymphoma 6C3HED and leukemia L1210 and P388 in mice, hepatomas in rats and vaccina virus in HeLa cells;

b. is effective in preventing the growth of various Gram-positive bacteria and yeasts;

c. can be isolated as a yellow microcrystalline powder;

d. is soluble in organic solvents such as methanol, chloroform, ethanol, ethyl acetate, acetone and benzene, slightly soluble in water, but insoluble in ether, hexane and petroleum ether;

e. has a melting point of 129° to 135° C., and is optically active with $[\alpha]_D^{24} = +29°$ (C: 1.0, $CHCl_3$);

f. exhibits ultraviolet and visible absorption maxima at 229.5, 258, 290 and 434 nm in methanol; 229.5, 258, 290 and 434 nm in 0.1 N HCl-methanol; 239.5, 288, 314 and 523 nm in 0.1 N NaOH-methanol;

g. exhibits characteristic maxima in the infrared absorption spectrum at 3300, 3080, 2940, 2860, 1740, 1640, 1620, 1540, 1460, 1450, 1415, 1385, 1295, 1250, 1220, 1195, 1165, 1125, 1105, 1090, 1010, 960, 930, 890, 840, 815, 760, 730, 580 and 450 $cm^{-1}$;

h. gives upon acid hydrolysis rhodosamine, 2-deoxyfucose, cinerulose A, 1-deoxyprromycin and alkavinone;

i. is a weakly basic anthracycline glycoside having the empirical formula of $C_{42}H_{54}NO_{15}$;

and the antitumor antibiotic aclacinomycin B which:

a. is effective in inhibiting the growth of leukemia L1210 and P388 in mice and vaccinia virus in HeLa cells;

b. is effective in inhibiting the growth of Gram-positive bacteria and yeasts;

c. can be isolated as a yellow microcrystalline powder;

d. is soluble in methanol, ethyl acetate, chloroform, ethanol, acetone and benzene, slightly soluble in water, but insoluble in ether, cyclohexane, hexane and petroleum ether;

e. has a melting point of 135° to 145° C., and is optically active with $[\alpha]_D^{24}$ +3° (C: 1.0, CHCl$_3$);

f. exhibits ultraviolet and visible absorption maxima at 229.5, 257,5, 290 and 433 nm in methanol, 229.5, 257.5, 290 and 433 nm in 0.1 N HCl-methanol, 238, 286 to 289, 315 and 525 nm in 0.1N NaOH-methanol;

g. exhibits characteristic maxima in the infrared absorption spectrum at 3300, 3070, 2940, 2850, 2750, 1740, 1640, 1620, 1540, 1465, 1445, 1410, 1380, 1290, 1245, 1215, 1160, 1120, 1095, 1050, 1010, 960, 920, 880, 840, 820, 805, 750, 725, 700, 600, 580 and 450 cm$^{-1}$;

h. gives aklavinone, rhodosamine, 2-deoxyfucose, 1-deoxy-pyrromycin and the same methylated disaccharide as cinerubin B on acid hydrolysis or partial hydrolysis in methanol;

i. is a weakly basic anthracycline glycoside having the empirical formula of $C_{42}H_{52}NO_{15}$.

There is further provided by the present invention the process for producing the antitumor antibiotics aclacinomycins A and B which comprises culturing an aclacinomycin-producing strain of *Streptomyces galilaeus having the identifying characteristics of A.T.C.C. 31133* under submerged aerobic conditions in a nutrient medium containing carbon sources and nitrogenous nutrients until a substantial amount of aclacinomycin A and B is produced by the said organism in the said nutrient medium and preferably by culturing in a nutrient medium at a temperature in the range of 20° to 35° C. or better yet at a temperature in the range of 25° to 30° C. with the pH from 5 to 8 and then, if desired, recovering the aclacinomycins from the culture medium by a process which includes at least one process selected from the group consisting of solvent extraction, solvent precipitation, concentration, gel filtration, counter current distribution, chelation with metal ions and adsorption followed by elution from an ion exchange resin, adsorbent siliceous earth material or synthetic adsorbent.

The processes of this invention include a process in which the solution containing aclacinomycins is freeze-dried and a process in which the solution containing aclacinomycins is freeze-dried after addition of at least one substance selected from the group consisting of deoxy-ribonucleic acid, glycerol, sugars, amino acids, inorganic and organic acids.

DETAILED DESCRIPTION

Aclacinomycin A and B markedly prolong the lives and improve the condition of mice inoculated with leukemia L1210 and P388 and lymphoma 6C3HED cells, and exhibit high lethal dose (LD$_{50}$) on rats, mice and rabbits and extremely low cardiotoxicity on hamsters. More particularly, the substances caused a remarkable inhibitory effect on the growth of various tumor cells in culture resulting from specific inhibition on RNA synthesis, and have also strong antimicrobial activity against bacteria and yeasts.

Figure 1:
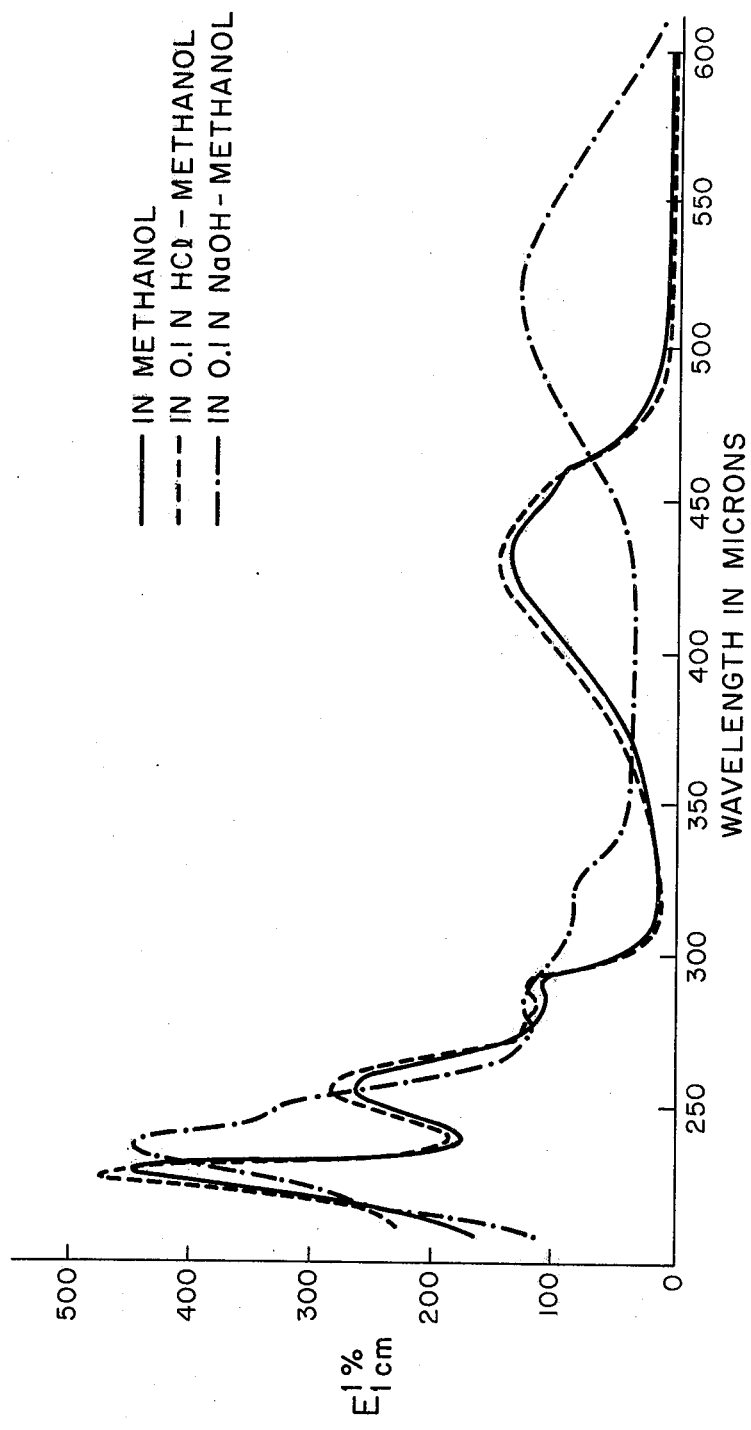
FIG. 1 shows ultraviolet absorption spectrum of aclacinomycin A in methanol, 0.1 N HCl-methanol and 0.1 N NaOH-methanol.
Figure 2:
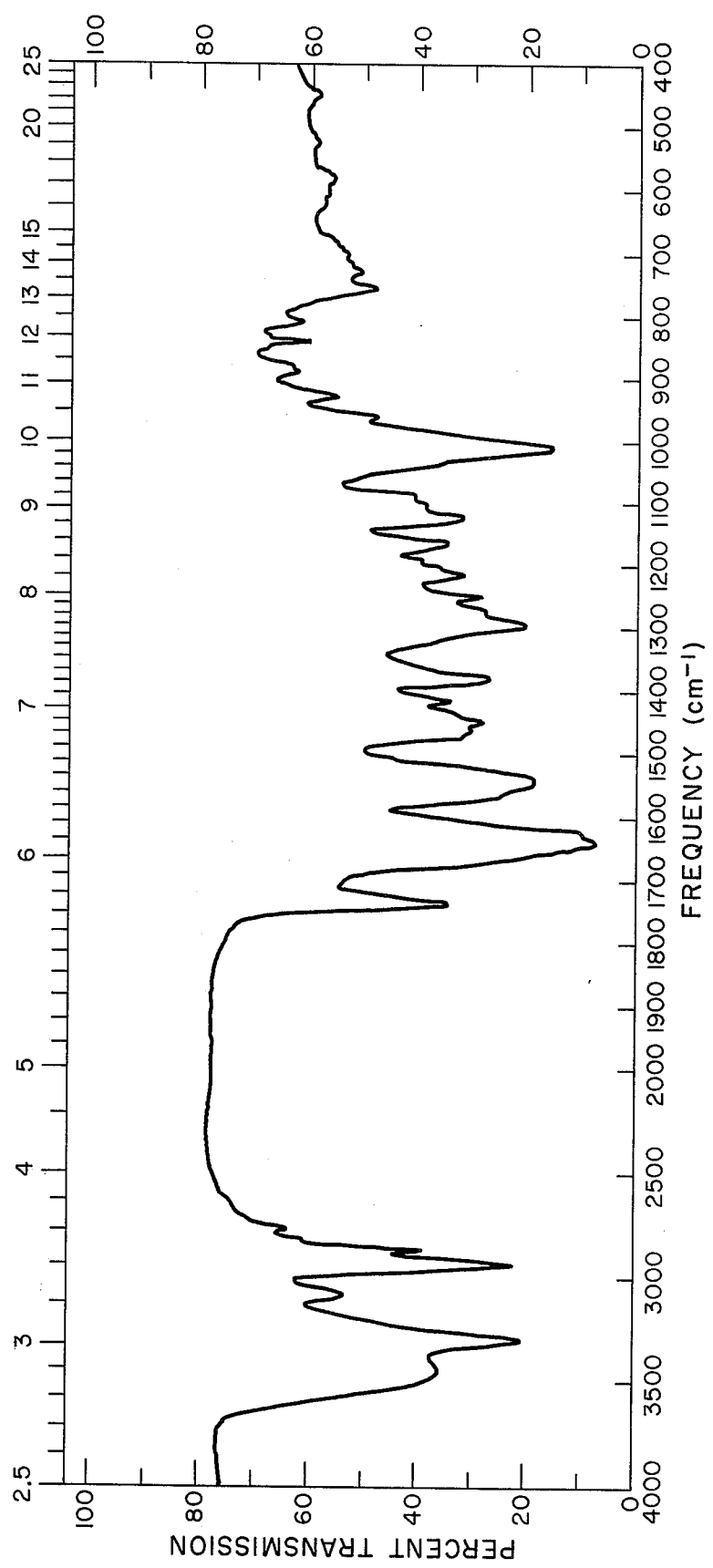
FIG. 2 is the infrared absorption spectrum of aclacinomycin A in potassium bromide.
Figure 3:
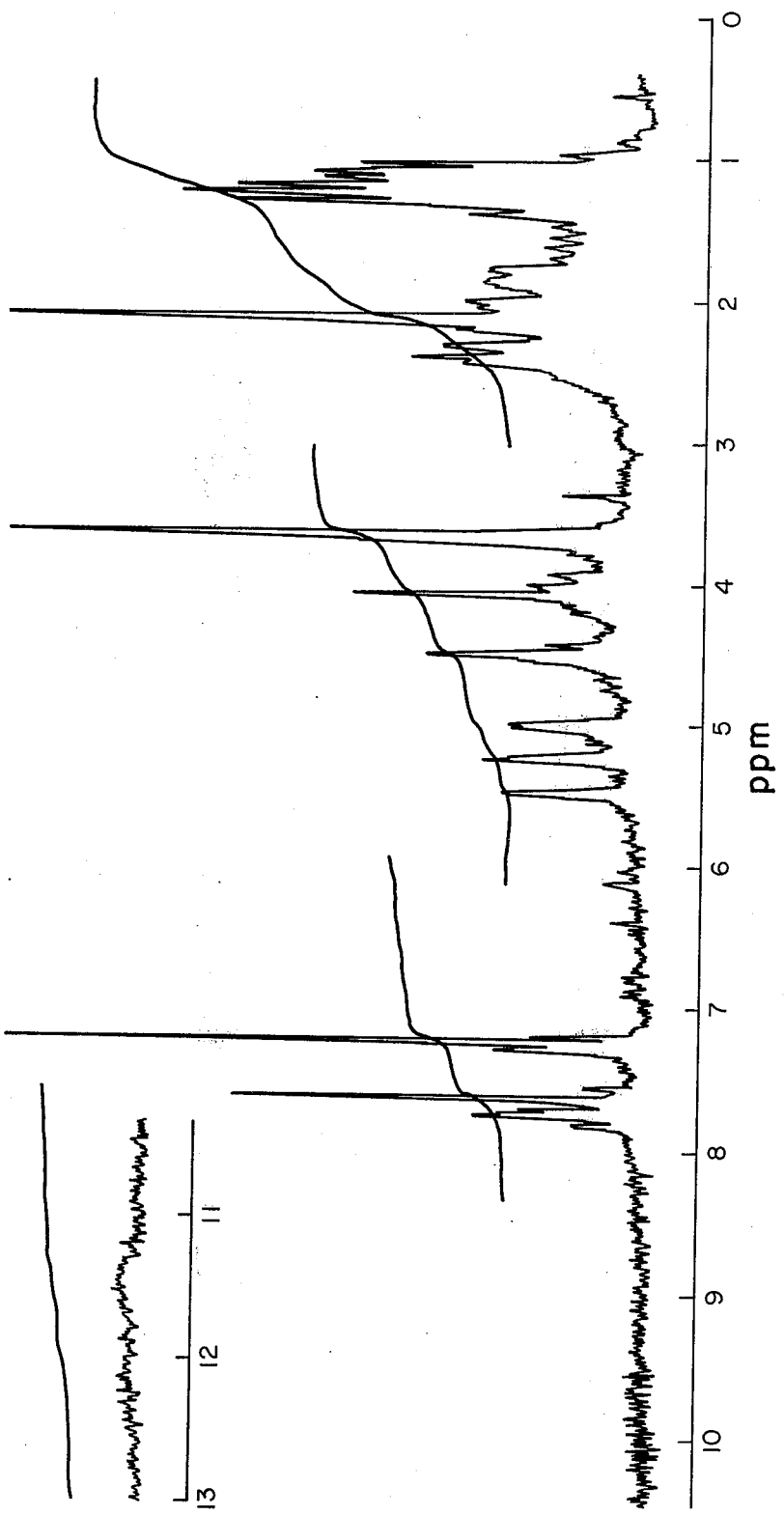
FIG. 3 is the NMR spectrum of aclacinomycin A in CDCl$_3$ (100 MHz).
Figure 4:
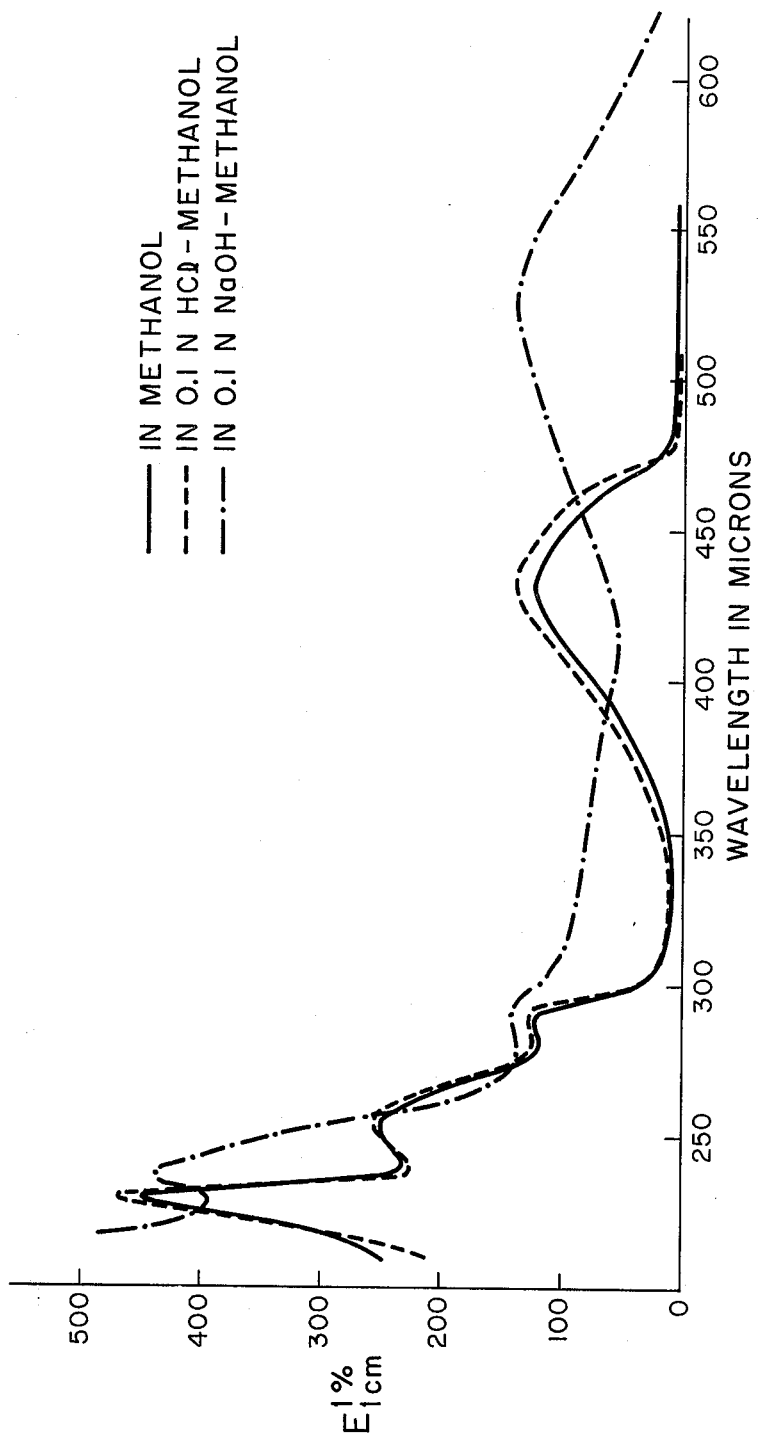
FIG. 4 is ultraviolet absorption spectrum of aclacinomycin B in methanol, 0.1 N HCl-methanol and 0.1 N NaOH-methanol
Figure 5:
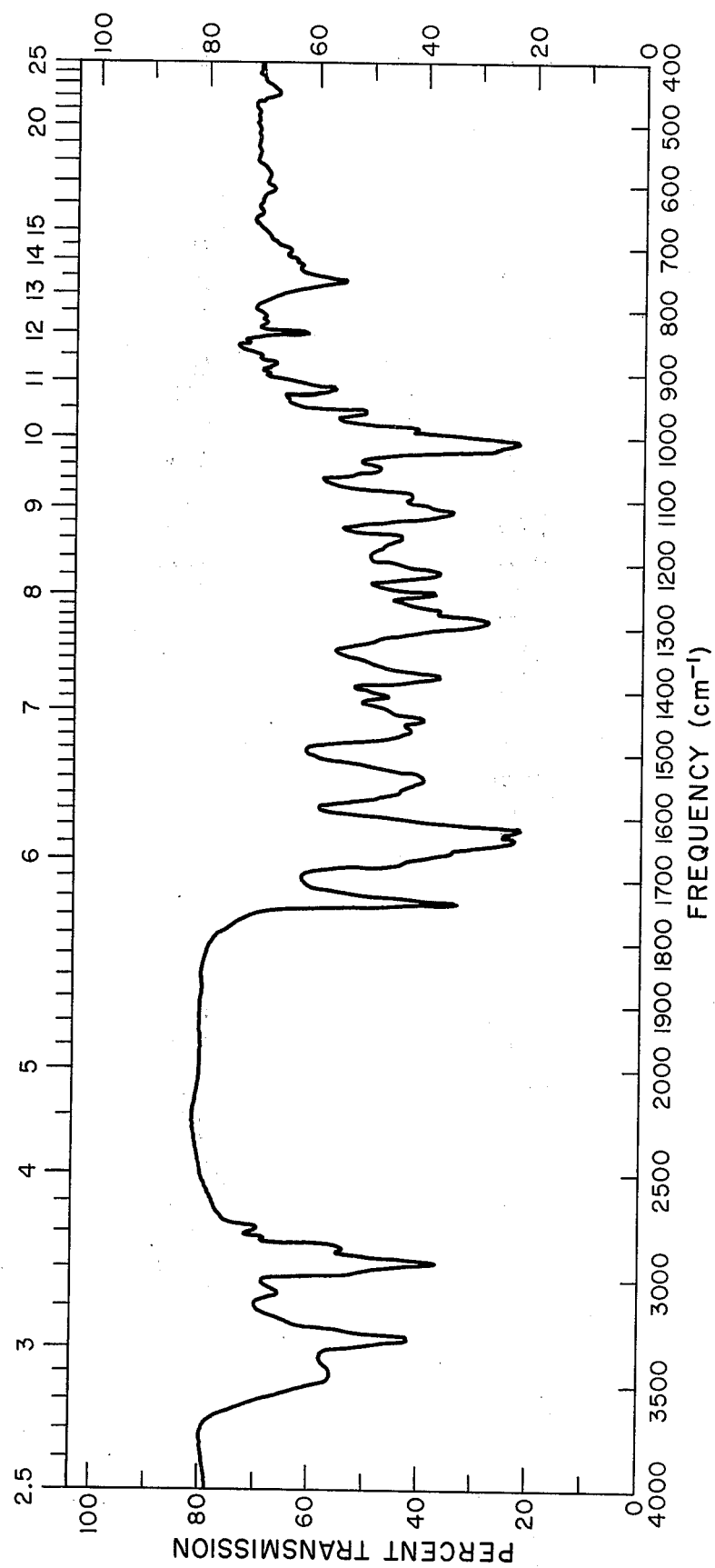
FIG. 5 shows the infrared absorption spectrum of aclacinomycin B in potassium bromide.
Figure 6:
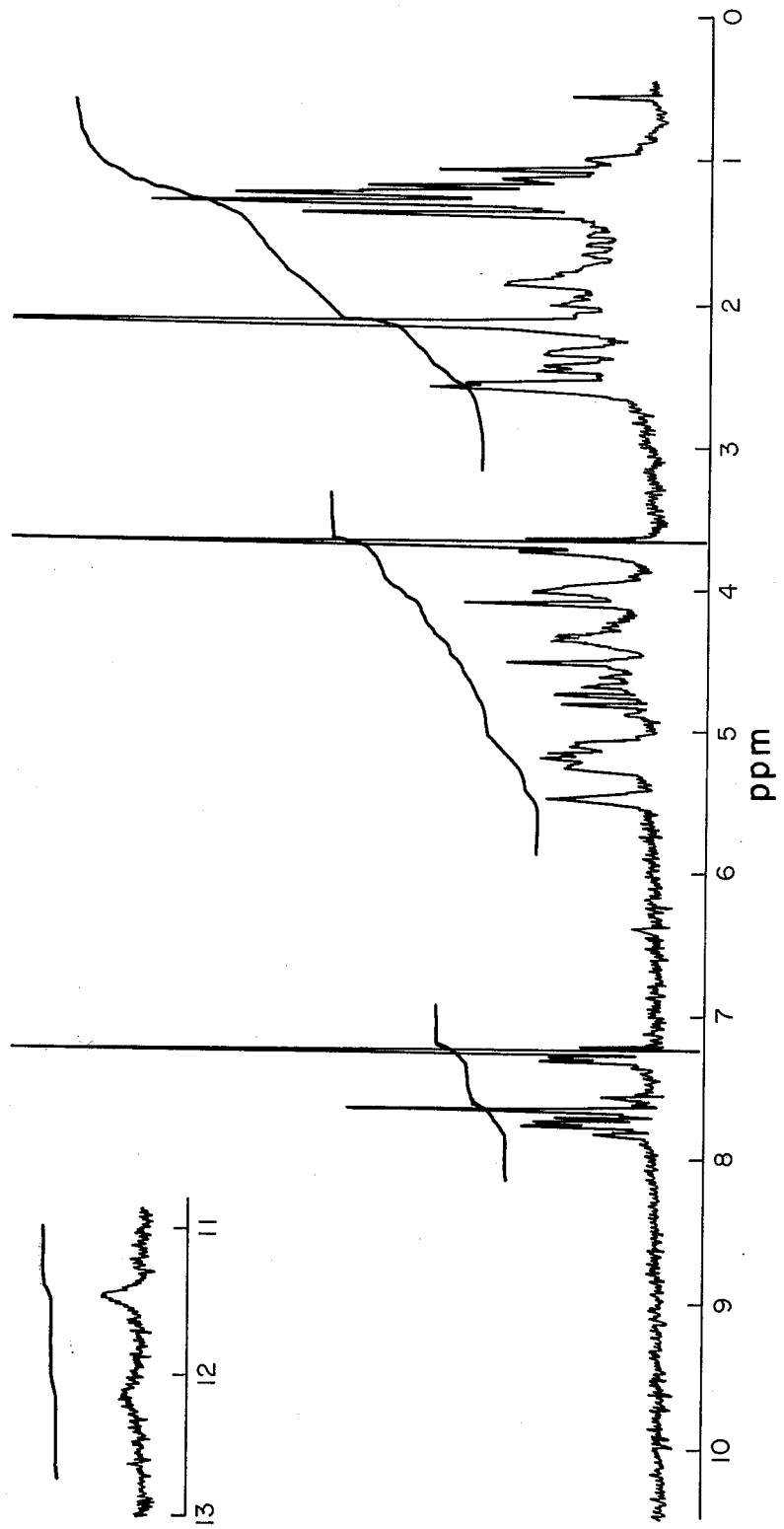
FIG. 6 is the NMR spectrum of aclacinomycin B in CDCl$_3$ (100 MHz).

Aclacinomycin A and B are obtained as yellow microcrystalline powders which have the empirical formulae of $C_{42}H_{54}O_{15}N$ and $C_{42}H_{52}O_{15}N$, respectively, and yield aklavinone, rhodosamine, 2-deoxyfucose, 1-deoxypyrromycin and cinerulose A from aclacinomycin A, and aklavinone, rhodosamine, 2-deoxyfucose, 1-deoxypyrromycin and the same methylated disaccharide as cinerubin B from aclacinomycin B on acid hydrolysis or partial hydrolysis in methanol, said substances being soluble in methanol, ethanol, chloroform, acetone, ethyl acetate, benzene and the like, slightly soluble in water, but insoluble in hexane, cyclohexane, ether and petroleum ether, exhibiting characterisitc absorption maxima in the infrared region when pelleted with potassium bromide and in ultraviolet and visible light as shown in FIGS. 1, 2 4 and 5 having NMR absorption spectra substantially as shown in FIGS. 3 and 6, having specific rotation in chloroform and melting point respectively of +29° and 129° to 135° C. for aclacinomycin A and +3° and 135° to 145° C. for aclacinomycin B, respectively.

There is further provided according to the present invention the process for the production of the antitumor antibiotics aclacinomycins A and B which comprises culturing a strain of *Streptomyces galilaeus* in an aqueous medium containing carbon sources and nitrogen sources under aerobic conditions until a substantial amount of aclacinomycins is accumulated in said solution, and then recovering said aclacinomycins from said solution using the methods of adsorption to ion-exchanger, adsorbent siliceous earth material and synthetic adsorbents, solvent extraction, solvent precipitation, counter-current distribution, etc. and combinations of these methods.

Although a number of anthracycline glycoside antibiotics are well known, e.g. adriamycin, daunomycin, carminomycin, rhodomycin, pyrromycin, aklavin etc., the aclacinomycins produced by the process of this invention are clearly different from any of them in the characteristics of molecular formula, degradation products on acid hydrolysis, ultraviolet, visible, infrared and NMR absorption spectra and the like, as described above. Moreover, their high antitumor activity and remarkably low cardiotoxicity are characteristics not exhibited by any of the anthracycline glycoside antitumor antibiotics.

The organism producing the antibiotics aclacinomycins A and B of the present invention was isolated from a soil sample collected at Osaki, Shinagawa-ku, Tokyo, Japan. A culture of MA144-M1 was deposited in the American Type Culture Collection, Rockville, Maryland and in the Fermentation Research Institute, Japan, and added to their permanent collections of microorganisms as A.T.C.C. No. 31133 and FERM No. 2455, respectively.

The strain No. MA144-M1 has the following properties:

1. Morphological properties:

Under the microscope, open spirals are observed to develop well from branched substrate mycelia. No whorls, and mature spore chain is moderately long with more than ten spores. The spores are ellipsoidal and measured 0.4 to $0.8\mu \times 0.8$ to $1.6\mu$, and its surface is smooth.

2. Properties on various media:

The description in parenthesis follows the color standard "Color Harmony Manual" published by Container Corporation of America, U.S.A.

a. On glucose-aspargine agar, incubated at 27° C. light yellowish brown growth (3gc, Lt. Tan); no aerial mycelium; no soluble pigment.

b. On sucrose-aspargine agar, incubated at 27° C. colorless or light yellowish brown growth (3gc, Lt. Tan); no aerial mycelium; no soluble pigment.

c. On glycerol-aspargine agar (ISP medium No. 5), incubated at 27° C.: yellowish orange (4ic, SUntan) to brown (51 g., Cocoa Brown) growth; white to light gray (2fe, Covert Gray) aerial mycelium; brown soluble pigment.

d. On starch-inorganic salts agar (ISP medium No. 4), incubated at 27° C.: Pale orange (3ea, Lt. Melon Yellow) to pale yellowish brown (3ie, Camel) growth; light gray (2fe, Covert Gray) to gray (e, Gray) aerial mycelium; brown soluble pigment.

e. On tyrosine agar (ISP medium No. 7), incubated at 27° C.: Brownish gray (3li, Beaver) to brown (4lg, Toast tan) aerial mycelium, black soluble pigment.

f. On nutrient agar, incubated at 27° C.: Colorless to grayish brown growth; no aerial mycelium, brown soluble pigment.

g. On yeast extract-malt extract agar (ISP medium No. 2), incubated at 27° C.: Light brown (4le, Maple) to brown (4ng, Lt. Brown) growth; light gray (3fe, Silver Gray) to gray (3ih, Beige Gray) aerial mycelium; brown soluble pigment.

h. On oatmeal agar (ISP medium No. 3), incubated at 27° C.; colorless to pale yellowish brown (2gc, Bamboo) growth; light gray (3fe, Silver Gray) aerial mycelium; brown soluble pigment.

i. On glycerol-nitrate agar, incubated at 27° C.: Colorless to pale yellowish brown (3gc, Lt. Tan) or light olive gray (2 db, parchment) growth; no aerial mycelium; no soluble pigment.

j. On starch agar, incubated at 27° C.: Pale yellowish brown (3gc, Lt. Tan) growth; gray (e, Gray) aerial mycelium; slight brown soluble pigment.

k. On calcium malate agar, incubated at 27° C.: Colorless growth; grayish white (b, Oyster white) to light brownish gray (3dc, Natural) aerial mycelium; no soluble pigment.

l. On gelatin stab, incubated at 20° C.: Pale brown to pale yellowish brown growth; white aerial mycelium; brown soluble pigment.

m. On glucose-peptone-gelatin stab, incubated at 27° C; Pale brown to brown growth; no aerial mycelium; brown soluble pigment.

n. On skimmed milk, incubated at 37° C.: Pale brown to brown growth; no aerial mycelium; brown soluble pigment.

3. Physiological properties:

a. Growth temperature was examined on maltose-yeast extract agar (maltose 1.0%, yeast extract 0.4%, agar 3.5%, pH 6.0) at 20, 24, 27, 30, 37 and 50° C. Optimal temperature for the growth is 27° to 37° and no growth at 50° C.

b. Gelatin liquefaction on 15% gelatin stab at 20° C.: and on glucose-peptone-gelatin stab at 27° C.: On the former medium, gelatin liquefaction was observed weakly on the 14 days-incubation, but on the latter weak or moderate liquefaction after 7 days incubation.

c. Starch hydrolysis on starch-inorganic salts agar at 27° C: Weak hydrolysis was observed after 5 days incubation.

d. Peptonization and coagulation of skimmed milk at 37° C: Moderate to strong peptonization began after 5 days incubation and finished on around 17 days. No coagulation.

e. Melanin formation on tyrosine agar (ISP medium No. 7), tyrosine-yeast extract broth (ISP medium No. 1) and peptone-yeast extract-ferrous agar (ISP medium No. 6) at 27° C.: positive on all media.

f. Liquefaction of calcium malate on calcium malate agar at 27° C.: Strongly positive.

g. Nitrate reduction on peptone agar containing 1.0% sodium nitrate (ISP medium No. 8) at 27° C.: Positive.

h. Utilization of carbohydrates of Pridham-Gottlieb basal medium (ISP medium No. 9), incubated at 27° C.: Abundant growth with L-arabinose, D-xylose, glucose, D-fructose, sucrose, inositol, L-rhamnose and raffinose; no growth with D-mannitol.

Summarizing the above characteristics of No. MA144-M1, the strain belongs to the genus Streptomyces and chromogenic type, and produces brown soluble pigment on various agar media. Aerial mycelium forms open spirals, but no whorls. The spore surface is smooth. The growth on various media is found to be pale yellowish brown to brown in general, but olive in a few medium, and aerial mycelium is light gray. Nitrate is reduced to nitrite. Proteolytic action is weak to moderate and starch hydrolysis is relatively weak. Melanin is produced on tyrosine agar, tyrosine-yeast extract broth and peptone-yeast extract-ferrous agar.

Among known species of Streptomyces, strain No. MA-144-M1 resembles *Streptomyces galilaeus*. Reference 1: Archiv fur Mikrobiolgie, 31, 356, 1958. Reference 2: International Journal of Systematic Bacteriology, 22, 298, 1972. With particular attention to differentiation based on the morphology, color of the aerial mycelium and other physiological properties, the difference between the present strain and the standard strain of *S. galilaeus* ISP 5481 obtained was investigated by parallel cultures. The results are as follows:

|  | MA144-M1 | Streptomyces galilaeus ISP 5481 | Reference 1 | Reference 2 |
| --- | --- | --- | --- | --- |
| Spore surface | smooth | smooth | smooth | smooth |
| Spore chain | open spirals | spirals | spirals | spirals |
| Aerial mycelium | light gray | light gray | grayish white to gray | gray |

-continued

|  | MA144-M1 | Streptomyces galilaeus ISP 5481 | Reference 1 | Reference 2 |
|---|---|---|---|---|
| Growth | pale yellowish brown to brown, sometimes light olive | pale yellowish brown-grayish brown-light olive gray | pale yellow to deep ruby red | grayish yellow -yellowish brown-olive brown |
| Soluble pigment | brown | brown | pale brown | pale yellow |
| Melanin formation: |  |  |  |  |
| ISP medium No. 1 | positive | positive | positive | positive |
| ISP medium No. 6 | positive | probably | positive | positive |
| ISP medium No. 7 | positive | positive | positive | positive |
| Starch hydrolysis | weak | weak | weak | * |
| Liquefaction of gelatin: |  |  | weak |  |
| Gelatin stab | weak | weak |  |  |
| Glucose-peptone-gelatin stab | weak to moderate | weak to moderate |  |  |
| Peptonization of milk | moderate to strong | Moderate | negative | * |
| Coagulation of milk | negative | negative | weak | * |
| Nitrate reduction | positive | positive | * | * |
| Utilization of carbohydrates: |  |  | * |  |
| L-Arabinose | positive | positive |  | positive |
| D-Xylose | positive | positive |  | positive |
| Glucose | positive | positive |  | positive |
| D-Fructose | positive | positive |  | positive |
| Sucrose | positive | positive |  | positive |
| Inositol | positive | positive |  | positive |
| L-Rhamnose | positive | positive |  | positive |
| Raffinose | positive | positive |  | positive |
| D-Mannitol | negative | negative |  | negative |

* no data

From the results, the present strain agrees very closely with S. galilaeus ISP 5481 in morphology and color of the growth and mycelium on various media and physiological properties. Furthermore, similarity of both strains exists in the fermentation products; that is, cinerubin which can be produced by S. galilaeus is one of the by-products of the present strain. Thus, strain No. MA144-M1 can be identified as Streptomyces galilaeus.

Since the Streptomyces are easily mutatable naturally or artificially, S. galilaeus No. MA144-M1 in the present invention includes the typical strain described above and all natural and artificial variants and mutants thereof. That is, S. galilaeus No. MA144-M1 of the present invention includes all strains producing aclacinomycin. As with the known antibiotics it is anticipated that higher production of aclacinomycin can be achieved by the selection of highly productive strains after single colony selection, by the treatment of an aclacinomycin-producing strain with various mutagens, or by the genetic procedures of recombination, transformation or transduction.

Aclacinomycins are produced by the cultivation of S. galilaeus under suitable conditions. The general procedures used for the cultivation of other actinomycetes are applicable to the cultivation of S. galilaeus. A fermentation broth containing aclacinomycin is prepared by inoculating spores or mycelia of the aclacinomycin-producing organism into a suitable medium and then cultivating them under aerobic conditions. Although cultivation on a solid medium is possible for the production of aclacinomycin, submerged aerobic culture is especially advantageous for production of large quantities of the antibiotics. Media consisting of known kinds of nutritional sources for actinomycetes are useful. The medium preferably contains commercially available products such as glycerol, glucose, starch, dextrin, maltose, molasses, oils, fats, lipids and the like as carbon sources in either purified or crude state, and as the nitrogen sources, commercially available products such as soybean meal, malt extract, peptone, yeast extract, distiller's solubles, fish meal, gluten meal, corn steep liquor, cottonseed flour, casein, hydrolyzed protein substances, nitrates, ammonium salts, urea and the like, and inorganic salts such as sodium chloride, potassium chloride, potassium phosphate, magnesium sulfate, calcium carbonate and trace amounts of heavy metal salts such as copper, zinc, manganese, iron, and the like. In the aerated submerged culture an antifoam such as liquid paraffin, soybean oil, fat or silicone is used. Any fermentation temperature can be employed within the range, 20° to 35° C., in which an aclacinomycin-producing organism can grow, although the most preferred range of temperature is 25° to 30° C. The pH of the culture medium ranges from 5 to 8.0.

Unless it is otherwise specified, the method of cultivation and the assay method are as follows:

1. Shaking culture: 100 ml. of medium in a Sakaguchi flask or 50 ml. of medium in an Erlenmeyer flask of 500 ml. is sterilized at 120° C. for 15 minutes. Spores or mycelia of an aclacinomycin-producing organism are inoculated into the sterilized medium from an agar slant culture by platinum loop and cultivated at 28° C. for 4 days on a reciprocal or rotary shaker.

2. Tank culture: 100 liters of medium are prepared in a 200 liter fermenter and sterilized at 120° C. for 15 minutes. The sterilized medium is inoculated with 2 liters of cultured broth which was previously shake-cultured for 2 days. The fermentation in the tank proceeds under aeration of 50 liters sterile air per minute, with stirring at 160 r.p.m. for 2 days. Silicone oil and liquid paraffin are used for defoamer.

3. Assay of aclacinomycin-TLC-chromatoscanner method; Aclacinomycins A and B extracted from the cultured broth, mycelia or culture filtrate by acetone, ethyl acetate or chloroform-methanol mixture are spotted on the silica gel plate (Kieselgel 60F$_{254}$, Merck Co.) with 5 mm in diameter. After 15 minutes saturation in the developing vessel, TLC plate is developed in acetone ascending to 15 cm at room temperature. Spots corresponding to aclacinomycin A and B are determined by optical density at 430 nm using a Shimadzu Dual-Wave length TLC Scanner, Model CS-900, under a certain condition, Zig-Zag scanning at 430 nm-700nm, 1.25 × 1.25 nm slit, 10 mm/min scan and chart speed. The standard curves of purified aclacinomycin A and B are previously prepared ranging from 0.2 to 15 mcg./spot.

The aclacinomycin-producing strain was first shake-cultured in the following medium.

The basal medium consisted of 1% glucose, 1% potato starch, 1.5% "Prorich" (soybean meal, the product of Ajinomoto Co.), 0.1% $KH_2PO_4$, 0.1% $MgSO_4.7H_2O$, 0.3% NaCl, 0.0007% $CuSO_4.5H_2O$, 0.0001% $FeSO_4.7H_2O$, 0.0008% $MnCl_2.4H_2O$ and 0.0002% $ZnSO_4.5H_2O$, and adjusted to pH 7.0.

The cultured broth at the 4th day exhibited the accumulation of 45 mcg./ml. of aclacinomycin A and 15 mcg./ml. of aclacinomycin B.

Aclacinomycin A and B were produced in media containing various carbon and nitrogen sources under shaking conditions as shown by examples described as follows:

1. Various carbon sources were added to the basal medium consisting of 1.5% "Prorich" and other salts as follows:

|  | Aclacinomycin A present at indicated time | | | | | |
|---|---|---|---|---|---|---|
|  | 2 days | | 3 days | | 4 days | |
|  | pH | mcg/ml | pH | mcg/ml | pH | mcg/ml |
| 2% glucose | 7.3 | 27 | 7.4 | 38 | 8.0 | 41 |
| 2% maltose | 6.6 | 15 | 6.0 | 28 | 7.0 | 32 |
| 2% sucrose | 7.3 | 32 | 7.7 | 39 | 8.2 | 40 |
| 2% soluble starch | 7.4 | 35 | 7.4 | 28 | 7.9 | 33 |
| 2% potato starch | 7.2 | 36 | 7.6 | 33 | 8.1 | 42 |
| 1% glucose + 1% potato starch | 6.3 | 32 | 7.7 | 34 | 8.3 | 43 |
| 1% glucose + 1% maltose | 7.4 | 26 | 6.7 | 28 | 7.7 | 30 |
| 1% glucose + 1% sucrose | 7.3 | 26 | 7.6 | 30 | 7.8 | 32 |
| 1% glucose + 1% soluble starch | 7.1 | 37 | 7.9 | 37 | 8.4 | 39 |
| 1% glucose + 1% glycerol | 4.9 | 36 | 6.3 | 36 | 8.1 | 41 |

2. Various nitrogen sources were added to the basal medium consisting of 1% glucose, 1% potato starch and other salts as follows:

|  | Aclacinomycin A present at indicated time | | | | | |
|---|---|---|---|---|---|---|
|  | 2 days | | 3 days | | 4 days | |
|  | pH | mcg/ml. | pH | mcg./ml. | pH | mcg./ml. |
| 1.5% "Prorich" (soybean meal, Ajinomoto Co.) | 6.3 | 34 | 7.0 | 48 | 8.0 | 45 |
| 1.5% "Meat" (soybean meal, Ajinomoto Co.) | 5.8 | 37 | 7.1 | 54 | 8.1 | 48 |
| 1.5% malt extract | 6.2 | 9 | 6.6 | 7 | 6.6 | 13 |
| 1.5% yeast extract | 5.4 | 45 | 7.7 | 43 | 8.5 | 40 |
| 1.5% casamino acid | 6.9 | 18 | 8.0 | 21 | 8.3 | 22 |
| 1.5% beef extract | 5.6 | 9 | 7.2 | 32 | 8.2 | 36 |
| 1.5% polypeptone | 6.2 | 38 | 8.2 | 28 | 8.6 | 23 |

3. When the concentrations of carbon and nitrogen sources in the basal medium were varied, aclacinomycin A and B were accumulated as follows:

|  |  | Carbon source % | | | | | |
|---|---|---|---|---|---|---|---|
| Glucose |  | 1 | | 2 | | 3 | |
| Potato starch |  | 1 | | 2 | | 3 | |
|  |  | *A | B | A | B | A | B |
| "Prorich" | 1.5% | 33 | 23 | 36 | 19 | — | — |
|  | 2.5% | 31 | 39 | 39 | 28 | 51 | 34 |
| "Meat" | 1.5% | 32 | 19 | 48 | 31 | — | — |
|  | 2.5% | 17 | 24 | 43 | 28 | 58 | 29 |

*aclacinomycin A or B: mcg./ml.

The above results are merely examples, and it can be said that carbon sources such as glucose, starch, maltose and sucrose are favorable for the production of aclacinomycin and nitrogen sources such as soybean meal, yeast extract, beef extract and peptone are suitable.

When the fermentation was carried out at 28° C. with shaking using one of the suitable media at pH 6.9, i.e. 2% glucose, 2% potato starch, 2.5% "Meat", 0.1% $KH_2PO_4$, 0.1% $MgSO_4.7H_2O$, 0.0007% $CuSO_4.5H_2O$, 0.0001% $FeSO_4.7H_2O$, 0.0008% $MnSO_4.4H_2O$ and 0.0002% $ZnSO_4.5H_2O$, the pH of the medium dropped to 5.25 to 5.10 in 20 hours and the growth of mycelium increased at 10 hours after inoculation. Thereafter, pH rose to 7.0 to 7.5 on 3 days and aclacinomycin A and B reached a maximum, i.e. 46 mcg./ml. of A and 23 mcg./ml. of B in the broth. In order to isolate aclacinomycin, the antibiotic may be extracted with a suitable solvent either from the cultured broth "in toto" without filtering the mycelium mass or from the mycelium and the culture liquid previously separated by filtration. Most of the antibiotics exist in the filtration cake which consists of the mycelium admixed with the diatomaceous earth. Thereafter, the filtration cake is pulped and stirred in an organic solvent for the extraction of antibiotics. Suitable solvents are alcohols such as methanol, ethanol, butanol, ketones such as acetone, methyl ethyl ketone; halogenated hydrocarbons such as chloroform, methylene chloride, benzene or aqueous solutions of organic or inorganic acids such as acetic acid, hydrochloric acid, sulfuric acid. Preferred are acetone, ethyl acetate, mixtures of organic solvents such as alcohols and water-immiscible ketones and aqueous solution of inorganic or organic acids.

In order to extract the antibiotics in the filtrate, it is advantageous to add to the weakly acidified or neutralized filtrate a double volume of a water-immiscible organic solvent such as butanol, chloroform, ethyl acetate, butyl acetate or benzene. Among the separation methods for aclacinomycin, the effective one may be carried out by counter current distribution chromatography using silicic acid, alumina, Sephadex LH20 (Pharmacia Fine Chemicals AB, Uppsala, Sweden) or synthetic adsorbents, adsorption to active carbon and the like, and the combination of solvent extraction and these methods.

The antibiotics can be directly extracted from cultured broth by the above-mentioned methods without the separation of mycelium.

After concentrating in vacuo, the extracts are made at a pH between 5 to 7 and re-extracted with a water-immiscible solvent, for example, n-butanol, amyl alcohol, ethyl acetate, chloroform, benzene, methylene chloride, methyl propyl ketone and the like. From the water-immiscible organic solution the active crude substance is obtained as a yellow powder by concentration in vacuo to a small volume and precipitation with low polar solvents, for example, saturated hydrocarbons such as n-hexane, cyclohexane and petroleum ether or ethers such as diethyl ether and dipropyl ether.

To remove other pigmented substances such as cinerubin A and B from the active crude substance and to obtain pure aclacinomycin A and B, further purification may be carried out by column chromatography using various adsorbents such as silicic acid, alumina, Sephadex LH20, by ion-exchangers such as weakly acidic resins and polystyrene-divinylbenzene cross-linked matrix resins such as Amberlite XAD, by chelation with various metals such as cupric, ferrous, ferric, calcium and magnesium ions, and by combinations of at least one or more processes selected from the methods of chelation with metal ions, solvent precipitation, solvent extraction, counter current distribution etc.

For example, when crude aclacinomycins A and B was dissolved in a small amount of chloroform, subjected to a silicic acid column and then eluted with chloroform-methanol mixture, aclacinomycin B fraction was eluted first with a 50:1 chloroform-methanol mixture and then aclacinomycin A was eluted with above mixture of 30:1 to 20:1. The eluates of aclacinomycins A and B were separately concentrated in vacuo, and were further separated completely from cinerubin A and B and a small amount of impure pigmented substances by means of synthetic adsorbent column chromatography, i.e., Column Lite ($Al_2O_3 \cdot MgO \cdot 2SiO_2 \cdot 4H_2O$, Fuji Chemical Co.), Floridil (Activated magnesium silicate, Floridin Co.), hydroxylapatite, or of the addition of $1 \times 10^{-3}$ to $1 \times 10^{-2}$ M $CuSO_4$, $FeCl_3$, $FeSO_4$ or $MgSO_4$ to make chelate complex of cinerubin A and B, followed by Sephadex LH 20 column chromatography. The resulting solutions of pure aclacinomycin A and B can be concentrated in vacuo to dryness, and also be lyophilized alone or with at least one substance selected from serum albumin, globulin, gelatin, glycerol, sugars, amino acids, inorganic or organic acids etc.

Aclacinomycins A and B obtained by a combination of the above-mentioned methods and described in the examples below was demonstrated to be pure and uniform by single spot on the thin-layer chromatography using various solvent systems, constant melting point and dextrorotation, elementary analysis, characteristic peaks on ultraviolet, visible, NMR and infrared absorption spectra, and has the following properties:

Aclacinomycin A:

Weakly basic and lipophilic yellow powder or microcrystalline powder. Elementary analysis yields the following values:

| Found | C = 62.37% | C = 62.05% |
|---|---|---|
| | H = 6.67% | H = 6.69% |
| | O = 29.38% | O = 29.52% |
| | N = 1.82% | N = 1.72% |
| Molecular weight = 813. | | |

The melting point and dextrorotation ($[\alpha]_D^{24}$) of its 1% solution in chloroform were 129° to 135° C. and +29° respectively. Its absorption spectra in the ultraviolet and in the visible ranges (FIG. 1) show bands at the following wave-lengths:

in methanol:
at 229.5 nm, $E_{1\ cm}^{1\%} = 540$
258 nm, $E_{1\ cm}^{1\%} = 301$
290 nm, $E_{1\ cm}^{1\%} = 128$
434 nm, $E_{1\ cm}^{1\%} = 147$ in 0.1 N HCl-methanol:
at 229.5 nm, $E_{1\ cm}^{1\%} = 578$
258 nm $E_{1\ cm}^{1\%} = 329$
290 nm $E_{1\ cm}^{1\%} = 141$
434 nm $E_{1\ cm}^{1\%} = 164$ in 0.1 N NaOH-methanol:
at 239.5 nm, $E_{1\ cm}^{1\%} = 678$
288 nm, $E_{1\ cm}^{1\%} = 232$
314 nm, $E_{1\ cm}^{1\%} = 156$
523 nm, $E_{1\ cm}^{1\%} = 170$ When pelleted with potassium bromide, characteristic absorption bands in the infrared spectrum (FIG. 2) are exhibited at the following wave numbers is $cm^{-1}$: 3300, 3080, 2940, 2860, 2760, 1740, 1640, 1620, 1540, 1460, 1450, 1415, 1385, 1295, 1250, 1220, 1195, 1165, 1125, 1105, 1090, 1010, 960, 930, 890, 840, 815, 760, 730, 580 and 450. Proton-NMR spectrum was recorded on a Varian XL-100-15 spectrophotometer operating in the Fourier transform mode at 100 MHz as shown in FIG. 3.

The antibiotic aclacinomycin A is soluble in methanol, ethanol, chloroform, ethyl acetate, acetone, benzene, dimethyl sulfoxide (DMSO) and methyl cellosolve, is slightly soluble in water, but is insoluble in ethyl ether, hexane, cyclohexane and petroleum ether. The aqueous solution is yellow and turns to reddish brown in concentrated sulfuric acid. With alcoholic magnesium acetate this solution shows a purplish red coloring and turns to red purple on alkalinization.

Aclacinomycin B:

Weakly basic, lipophilic and yellow powder or microcrystalline powder. Elementary analysis yields the following values:

| | | Calcd. for $C_{42}H_{52}NO_{15}$ |
|---|---|---|
| Found | C = 62.21% | C = 61.87% |
| | H = 6.46% | H = 6.29% |
| | O = 29.60% | O = 29.80% |
| | N = 1.73% | N = 1.89% |

|  | Calcd. for $C_{42}H_{52}NO_{15}$ |
|---|---|
| Molecular weight = 811 | |

The melting point is 135° to 145° C. and the dextrorotation ($[\alpha]_D^{24}$ in 1% chloroform) is +3°. The absorption spectra in the ultraviolet and in the visible ranges (FIG. 4) show bands at the following wave-lengths:
in methanol:
 at 229.5 nm, $E_{1\ cm}^{1\%} = 452$
 257.5 nm, $E_{1\ cm}^{1\%} = 261$
 290 nm, $E_{1\ cm}^{1\%} = 120$
 433 nm, $E_{1\ cm}^{1\%} = 120$
in 0.1 N HCl-methanol:
 at 229.5 nm, $E_{1\ cm}^{1\%} = 465$
 257.5 nm, $E_{1\ cm}^{1\%} = 261$
 290 nm, $E_{1\ cm}^{1\%} = 125$
 433 nm, $E_{1\ cm}^{1\%} = 134$
in 0.1 N NaOH-methanol:
 at 238 nm, $E_{1\ cm}^{1\%} = 440$
 286–289 nm, $E_{1\ cm}^{1\%} = 142$
 315 nm, $E_{1\ cm}^{1\%} = 97$
 525 nm, $E_{1\ cm}^{1\%} = 135$ Characteristic absorption bands in the infrared spectrum (FIG. 5) are exhibited at the following wave numbers in $cm^{-1}$ (KBr): 3300, 3070, 2940, 2850, 2750, 1740, 1640, 1620, 1540, 1465, 1445, 1410, 1380, 1290, 1245, 1215, 1160, 1120, 1095, 1050, 1010, 960, 920, 880, 840, 820, 750, 725, 700, 600, 580 and 450. NMR spectrum of aclacinomycin B is shown in FIG. 6.

The antibiotic is soluble in methanol, ethanol, chloroform, ethyl acetate, acetone and acidic water, is slightly soluble in water, but is insoluble in hexane, cyclohexane, and ethers. The aqueous solution is yellow and turns to deep reddish purple in concentrated sulfuric acid. This solution shows purplish red in alcoholic magnesium acetate, and gives red purple on alkalinization.

Aclacinomycins A and B have the following Rf values on silica gel thin-layer chromatograms using various solvent systems.

|  | Rf values of aclacinomycin | |
|---|---|---|
|  | A | B |
| Chloroform:methanol | | |
| 20:1 | 0.36 | 0.71 |
| 5:1 | 0.88 | 0.90 |
| Acetone | 0.43 | 0.72 |
| Acetone:hexane | | |
| 1:1 | 0.15 | 0.49 |
| Benzene:methanol | | |
| 1:1 | 0.86 | 0.93 |

On partial hydrolysis or methanolysis with dilute hydrochloric acid or in methanol containing 5% hydrochloric acid for 1 to 2 hours at room temperature, aclacinomycins A and B give methylated disaccharides and 1-deoxypyrromycin. Physicochemical properties such as absorption spectra of infrared, ultraviolet, visible ranges and NMR, melting point and dextrorotation of the methylated disaccharide obtained from aclacinomycin B coincided fully with those of the methylated disaccharide obtained from cinerubin B by partial acid hydrolysis (Helvetica Chimica Acta, 55, 467–480, 1972), and 1-deoxypyrromycin was also identified with the data of rhodomycin (Chem. Ber. 38, 1762, 1955, Naturwiss., 48, 716, 1961), cinerubin (Chem. Ber. 92, 1868, 1959) and pyrromycin (Chem. Ber. 92, 1904, 1959) on the basis of NMR spectrum, mass spectrum of aglycone, and the presence of rhodosamine in the acid hydrolysate.

Aclacinomycins A and B decompose into a neutral aglycone and two or three reducing sugars on hydrolysis with 0.3 N sulfuric acid for 3 hours at 85° C. The aglycone forms orange yellow crystals melting 171° to 174° C. and containing oxygen, carbon and hydrogen. Elementary analysis, infrared, ultraviolet and NMR spectra, fragment ion peaks of mass spectrum and other properties demonstrated that the aglycone of aclacinomycin A and B is aklavinone (Tetrahedron Letters, 8, 28, 1960, Naturwiss., 47, 135, 1960, Naturwiss. 42, 154, 1955, Naturwiss. 50, 92, 1963). Furthermore, according to the comparative analysis of sugars in the acid hydrolysates of aclacinomycin A and B and cinerubins A and B by thin-layer chromatography, aclacinomycin A has the same rhodosamine, 2-deoxyfucose, and cinerulose A as cinerubin A and aclacinomycin B has the same rhodosamine and 2-deoxyfucose as cinerubin B.

From the results mentioned above, the structures of aclacinomycins A and B in the present invention are as follows:

Structure of Aclacinomycin

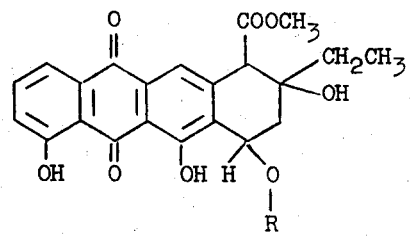

R =

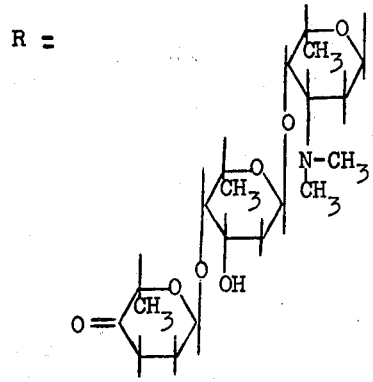

Aclacinomycin A

R =

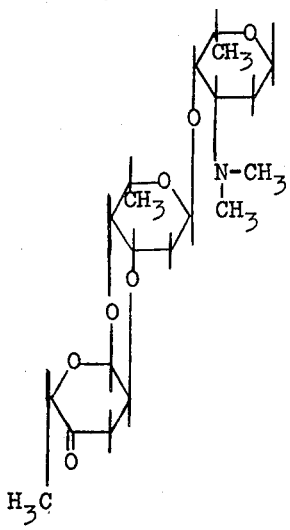

Aclacinomycin B

Aclacinomycins A and B (according to their physiochemical properties and structures as described above and by comparison with known antibiotics reported in the publications) belong to the group of anthracycline glycosides and are similar to cinerubins A and B, rutilantine, aklavin, requinomycin and galirubins.

Cinerubin and rutilantine are different from the present antibiotics in its aglycone, ε-pyrromycinonone (Tetrahedron Letters, 16, 17, 1959). Among the antibiotics having aklavinone aglycone, requinomycin (J. Antibiotics, 25, 393, 1972) and aklavin (J. Bacteriol., 72, 90, 1956) are not identical with the present antibiotics in the sugar moiety and molecular formula based on elementary analysis. Galirubins which are produced by Streptomyces galilaeus are most similar to the present antibiotics. K. Eckardt has reported that four components of galirubin (galirubin D, C, B and A) have been isolated from the mycelium of S. galilaeus and that galirubin A was ε-pyrromycinone glycoside, B was aklavinone glycoside, galirubinone C was ζ-pyrromycinone and galirubinone D was 7-deoxy aklavinone. In respect of the physicochemical properties of galirubin B which has aklavinone as its aglycone, the report has not clearly presented its detailed purification procedure, chromatographic behavior, melting point, elementary analysis, absorption spectra of infrared, ultraviolet, visible ranges, and NMR, and only elucidated that two sugar spots were detected in the acid hydrolysate of galirubin B on the paper chromatogram.

Thus aclacinomycins A and B, having aklavinone aglycone and three sugars, is clearly differentiated from galirubin B as in the above stated properties. It is verified that the present antibiotics are new substances discovered by the present inventors.

Therapeutically useful non-toxic salts and deoxyribonucleic acid (DNA)-complexes of the antibiotics aclacinomycins A and B can be derived from organic and inorganic acid, for example, hydrochloric acid, phosphoric acid, sulfuric acid, acetic acid, propionic acid, oleic acid, palmitic acid, citric acid, succinic acid, glutamic acid, pantothenic acid and DNA obtained from calf thymus, HeLa cell, human embryonic cell, E. coli and other animals and microorganisms.

Biological activities of aclacinomycins A and B are as follows:

1. The antimicrobial spectrum of aclacinomycins A and B was determined by the broth dilution method as follows:

| Antimicrobial spectrum of aclacinomycins A and B | | |
|---|---|---|
| | Minimum Inhibitory Concentration (mcg./ml) | |
| Test organism | A | B |
| Bacillus subtilis ATCC 6633 | <0.2 | <0.2 |
| B. cereus ATCC 9634 | <0.2 | <0.2 |
| B. megaterium | <0.63 | <0.2 |
| Staph. aureus FDA 209P | <0.63 | <0.2 |
| Staph. aureus Smith | <0.2 | <0.2 |
| Sar. lutea ATCC 9341 | <0.2 | <0.2 |
| Mic. flavus | <0.2 | <0.2 |
| Cory. bovis 1810 | <0.2 | <0.2 |
| Mycobact. smegmatis ATCC 607 | 2.5 | 5 |
| Strept. faecalis | 2.5 | 2.5 |
| St. pyogenes NY 5 | 1.25 | 1.25 |
| Diplo. pneumoniae Type 1 | 0.63 | 0.63 |
| Diplo. pneumoniae Type 3 | 0.63 | 0.63 |
| E. coli K12 | >100 | >100 |
| Kl. pneumoniae ATCC 10031 | >100 | >100 |
| Ps. aeruginosa A20229 | >100 | >100 |
| Can. albicans IAM 4905 | 10 | 10 |
| Can tropicalis IAM 4924 | 20 | 20 |

2. Antitumor effects: Furthermore, the antibiotics aclacinomycin A and B show marked inhibitory effects on experimental animal tumors of ascitic and solid tumors. This antitumor action can be most significantly demonstrated in leukemia in mice and hepatomas in rats. For example, when $BDF_1$ mice weighing 18 to 22 grams are inoculated with $1 \times 10^6$ cells of P388 cells or $5 \times 10^5$ cells of L1210 cells intraperitoneally and aclacinomycin A and B and aclacinomycin A-DNA complex are administered intraperitoneally once daily for 10 days consecutively 24 hours after the inoculation, the survival time of the mice is prolonged remarkably at the rate of over 150% in a dosage range of 0.5 to 5 mg./kg. of body weight per day compared with control mice receiving no antibiotic, as shown in the following table:

| Antibiotic | Dose (mg./kg./day) | Mean survival time (days) | T/C (%) | 30 day survivors |
|---|---|---|---|---|
| Aclacinomycin A | 4.0 | 21.5 | 215 | 1/4 |
| | 2.0 | 30.0 | 300 | 4/4 |
| | 1.0 | 28.0 | 280 | 3/4 |
| | 0.5 | 23.0 | 230 | 2/4 |
| Aclacinomycin B | 4.0 | 8.5 | 85 | 0/4 |
| | 2.0 | 17.5 | 175 | 0/4 |
| | 1.0 | 19.0 | 190 | 1/4 |
| | 0.5 | 14.7 | 147 | 0/4 |
| Aclacinomycin A-DNA complex | 4.0 | 19.0 | 190 | 1/4 |
| | 2.0 | 30.0 | 300 | 4/4 |
| | 1.0 | 30.0 | 300 | 4/4 |
| | 0.5 | 27.3 | 273 | 3/4 |
| control | — | 10.0 | — | 0/8 |

When CH3/He mice weighing 20 to 23 grams are inoculated with $1 \times 10^7$ cells of lymphoma 6C3HED-/OG intraperitoneally or with $5 \times 10^6$ cells of lymphoma 6C3HED/OG subcutaneously and aclacinomycin A is administered intraperitoneally once daily for 10 days consecutively 3 hours after the inoculation, aclacinomycin A shows marked inhibition of the growth of ascitic or solid 6C3HED/OG tumor as shown in the following table.

3. Acute toxicity: $LD_{50}$'s upon a single injection of aclacinomycin A or B are summarized in the following table:

| Animal Species | Route | $LD_{50}$ (mg./kg.) A | B |
|---|---|---|---|
| Mouse | intravenous | 33.7 | 16.4 |
| Mouse | intraperitoneal | 22.6 | 13.7 |
| Rat | intravenous | 32.5 | 15.0 |
| Rat | intraperitoneal | 25–50 | 10–15 |

| | | Aclacinomycin A, Dose: mg./kg./day | | | | |
|---|---|---|---|---|---|---|
| | | 4 | 2 | 1 | 0.5 | control |
| Solid type: | Tumor weight (mg) | 5023 | 4633 | 2501 | 3695 | 7045 |
| | Tumor weight Body weight (%) | 19.5 | 15.1 | 9.5 | 12.4 | 29.6 |
| | Inhibition (%) | 28.7 | 34.2 | 64.5 | 47.6 | — |
| | 21 day survivors | 0/3 | 3/3 | 3/3 | 3/3 | 7/9 |
| Ascitic type: | MST (days)* | 20.1 | 31.8 | 37.5 | 15.0 | 20.5 |
| | T/C (%)** | 98 | 155 | 183 | 73 | — |
| | 62 day survivors | 0/3 | 0/3 | 1/3 | 0/3 | 0/3 |

*Mean survival time
**Survival ratio: Tested/control

Mice are inoculated intraperitoneally with a suspension of L1210 leukemia cells and treated with solutions of different concentrations of aclacinomycin A and 1,5 and 9 days following the tumor implantation. The following table, where the obtained results are summarized, shows that aclacinomycin A, administered in doses of 6 and 3 mg./kg./day, has increased considerably the mean survival time of the treated mice.

| Dose (mg/kg/day) | Mean Survival Time (days) | 30 day survivors |
|---|---|---|
| 12 | 16.1 | 0/5 |
| 6 | 21.7 | 2/5 |
| 3 | 23.3 | 2/5 |
| 1.5 | 12.6 | 0/5 |
| Control | 10.4 | 0/10 |

Acute cardiac alterations in the electrocardiograms of hamsters were not induced by a single intravenous administration of 25 mg./kg. of aclacinomycin A or B.

4. The antibiotics inhibit the growth of cultured mammalian tumor cells, vaccinia virus in HeLa cells, and specifically the RNA synthesis at an extremely low concentration. When L1210 cells were inoculated in the medium, Rosewell Memorial Park Institute 1640, containing 10% calf serum and there were added various concentrations of aclacinomycin A and B, and as a precursor, $^{14}C$-thymidine, -leucine or -uridine and then incubated at 37° C. for 60 min. in the $^{14}C$-incorporation experiment and 3 days in the growth experiment, nucleic acid biosynthesis and cell growth were inhibited over 50% below 1 mcg./ml. aclacinomycin in the medium, as shown in the following table:

| | | $ID_{50}$ (mcg./ml.) | |
|---|---|---|---|
| | Aclacinomycin A | Aclacinomycin A-DNA complex* | Aclacinomycin B |
| L1210 cells: | | | |
| Growth | 0.12 | 0.08 | 0.24 |
| DNA synthesis | 1.1 | — | 4 |
| RNA synthesis | 0.1 | 0.2 | 0.2 |
| Protein synthesis | 6.3 | — | 12 |
| Vaccinia virus: | <10 | — | <10 |

*Calf thymus DNA, Type V (Sigma Co.) was used.

Donryu rats, grafted with ascitic hepatoma AH44 were treated intraperitoneally for 10 consecutive days with 2 mg./kg./day of aclacinomycin A. While the control rats had an average survival time of 14.5 days after the tumor implantation, all the treated rats were alive 30 days after the experiment.

In view of the aforesaid properties of the aclacinomycin A and aclacinomycin B substances, it has been confirmed that these substances are new antibiotics which are differentiated from any of the known antibiotics. According to a third aspect of this invention, there is provided a method for therapeutically treating a living animal, affected by leukemia, which comprises administering the aclacinomycin A substance and/or the aclacinomycin B substance to said animal in a dosage sufficient to reduce the affection by leukemia. According to a fourth aspect of this invention, there is further provided a pharmaceutical composition comprising the aclacinomycin A substance and/or the aclacinomycin B substance in an amount sufficient to reduce the affection by leukemia in vivo, the aclacinomycin A substance and/or the aclacinomycin B substance being in combination with a pharmaceutically acceptable carrier. It will be appreciated that the actual preferred amounts of the aclacinomycin substance used will vary according to the particular compound being used, the particular composition formulated, the mode of application and the particular situs and organism being treated. Many factors that modify the action of the drug will be taken into account by the skilled in the art, for example, age, body weight, sex, diet, time of administration, route of administration, rate of excretion, drug combinations, reaction sensitivities and severity of the disease. Optimal application rates for a given set of conditions can be ascertained by the skilled in the art using conventional dosage determination tests in view of the above guidelines.

Actual examples for the production and purification of aclacinomycins A and B are described below. The following examples are merely illustrative and it should be understood that our invention is not limited to these examples.

DESCRIPTION OF THE PREFERRED EMBODIMENTS

Example 1

An aqueous medium having the following composition was prepared:

|  | Percent |
| --- | --- |
| Potato starch | 1 |
| glucose | 1 |
| "Prorich" | 1.5 |
| $KH_2PO_4$ | 0.1 |
| $K_2HPO_4$ | 0.1 |
| $MgSO_4.7H_2O$ | 0.1 |
| NaCl | 0.3 |
| Minerals* | 0.125 |
| silicone (KM75) | 0.05 |
| pH | 7.0 |

*Minerals: $CuSO_4.5H_2O$ 2.8 g, $FeSO_4.7H_2O$ 0.4 g, $MnCl_2.4H_2O$ 3.2 g, $ZnSO_4.7H_2O$ 0.8 g, in 500 ml. water.

100 ml. of this medium was sterilized at 120° C. for 15 min. in a 500 ml. Sakaguchi-shaking flask which was inoculated from an agar slant culture of *Streptomyces galilaeus* MA144-M1 by platinum loop. Incubation proceeded for 48 hr. at 28° C. on a reciprocal shaker. Ten liters of the previously sterilized medium in a 20 liter stainless steel har fermenter were aseptically inoculated with 200 ml. of the above seed cultures. Fermentation was carried out at 28° C. for 32 hours with agitation (240 rpm) and aeration (5 l/min.). The cultured broth obtained was adjusted to pH 4.5, mixed with an adsorbent siliceous earth material and filtered from the mycelium. The filtrate and cake obtained thereby were extracted separately. The cake was suspended in acetone (3 liters per kg. wet cake), stirred for 2 hrs. and filtered, and the cake was further extracted with acetone once again. The extracts thus obtained were evaporated to one tenth volume in vacuo. The culture filtrate was adjusted to pH 6.8 and extracted twice with one third volume of ethyl acetate, and the ethyl acetate extracts were concentrated to one tenth volume in vacuo.

Twenty grams of the resulting oily substances were mixed with 20 grams of silicic acid (Mallinckrodt Chem. Co.), applied to a column 40 cm. in length and 4.5 cm. in diameter filled with silicic acid, and eluted with a benzene-acetone-methanol mixture. The initial eluate which eluted with a 1:1:0 mixture was discarded and the active fractions eluted with 1:3:0 and 1:3:0.3 mixtures were collected and concentrated to dryness in vacuo. 11.5 g. of this crude substance was then dissolved in a small amount of ethyl acetate and applied to the same silicic acid column as above. After discarding the initial eluates by the 1:1 and 2:1 benzene-acetone mixtures, aclacinomycin B fractions were first eluted with the above mixtures of 1:3 and 1:5 ratio, and aclacinomycin A fractions were then eluted with the 1:5:0.5 and 1:5:1 benzene-acetone-methanol mixtures. The eluates were dried over anhydrous sodium sulphate and concentrated to dryness in vacuo. 4.8 g. of crude aclacinomycin A and 3.5 g. of aclacinomycin B were obtained as yellow powder.

Example 2

2.0 g. of crude aclacinomycin B obtained as in Example 1 were mixed with 3 g. of silicic acid, subjected to a column 15 cm in length and 2 cm in diameter filled with 25 g. of silicic acid, and the aclacinomycin B fraction was eluted with chloroform containing 1% methanol and concentrated to a small volume in vacuo. From the concentrated solution by adding some n-hexane, 40 mg. of aclacinomycin B was obtained as yellow powder.

Example 3

2.0 g. of crude aclacinomycin A obtained as in Example 1 were dissolved in a small amount of chloroform, applied to a column 20 cm in length and 20 cm in diameter filled with 30 g. of silicic acid. After eluting off the pigments containing aglycone and aclacinomycin B and other impurities with chloroform and 1.5% methanol-containing chloroform, aclacinomycin A fractions were eluted with 2% methanol-containing chloroform, and concentrated to dryness in vacuo. 53 mg. of yellow powder of aclacinomycin A was obtained.

Example 4

Crude aclacinomycin A or B obtained as in Example 1 and 3 still contains a small amount of cinerubin A or B which was produced in the broth cultivated as in Example 1, and the impure cinerubin A or B can be removed by chelation with various metal ions.

250 mg. of crude powder of aclacinomycin A obtained as in Example 4 was dissolved in 20 ml. chloroform, and there was added 20 ml. of 1% $CuSO_4$ solution. After the solution was shaken strongly and stood for 1 hr, to the chloroform phase separated from the aqueous phase there was added $10^{-3}M$ EDTA (ethylenediamine tetraacetic acid) solution and that mixture was shaken vigorously for 1 min. and then the chloroform phase was separated and washed with water twice by shaking. The chloroform extract was dried over anhydrous sodium sulphate and concentrated in vacuo, and the addition of some n-hexane caused the precipitation of 120 mg. of pure aclacinomycin A.

Example 5

300 mg. of crude aclacinomycin B obtained as in Example 1 was dissolved in 10 ml. of methyl cellosolve and there was added 1 ml. of 100 mg./ml. $CuSO_4$ solution. After standing overnight, some precipitates were centrifuged off, and then the supernatant was concentrated to one-half volume in vacuo and chromatographed by using a column 100 cm in length and 4 cm in diameter filled with Sephadex LH20 in methanol. The initial impurities and purplish cinerubin B-Cu complex were discarded and subsequent yellow fractions were collected, added to $10^{-3}M$ EDTA solution and concentrated to one third in vacuo. Aclacinomycin B was extracted from the concentrate with chloroform and concentrated to dryness in vacuo. 128 mg. of pure aclacinomycin B was obtained.

Example 6

Aqueous medium having the following composition was prepared:

|  | Percent |
| --- | --- |
| potato starch | 2 |
| glucose | 2 |
| "Meat" | 2.5 |
| $KH_2PO_4$ | 0.1 |
| $K_2HPO_4$ | 0.1 |
| $MgSO_4.7H_2O$ | 0.1 |
| NaCl | 0.3 |
| $MnCl_2.4H_2O$ | 0.0005 |
| $FeSO_4.7H_2O$ | 0.0005 |
| silicone | 0.05 |
| pH | 7.2 |

Fifty ml. of this medium was sterilized at 120° C. for 15 min. in a 500 ml. Erlenmeyer flask which was inoculated with 1 ml. of frozen cultured broth of *Streptomyces galilaeus* MA144-M1. Incubation was carried out 48 hours at 30° C. on a rotary shaker. Ten liters of the same medium in a 20 liter stainless steel jar fermenter were aseptically inoculated with 200 ml. of the above cultures. After incubation at 30° C. for 18 hours with agitation (300 rpm) and aeration (5 l/min.), ten liters of the cultured broth were added to 600 liters of the above sterilized medium in a 1 kiloliter stainless steel tank and incubated at 30° C. for 48 hours with aeration (200 l/min.) and agitation (180 rpm). The cultured broth (570 l) obtained was adjusted to pH 5.0 with addition of 250 ml. of 30% $H_2SO_4$ mixed with an adsorbent siliceous earth material and the 53.5 kg. of cake so obtained was suspended in 70 l of acetone, stirred for 3 hours and filtered. The cake was further extracted with 85 liters of acetone once again. The extracts were evaporated to 40 liter in vacuo and added to 25 liter ethyl acetate. The ethyl acetate phase was separated and concentrated to 1 liter in vacuo. The crude aclacinomycin mixture which precipitated by adding 1 liter of n-hexane to the above concentrate was collected and washed with n-hexane-ethyl acetate mixture (50:1) twice, and 15.5 g. of orange yellow powder was obtained.

This crude powder was dissolved in 200 ml. of ethyl acetate and applied on a column 35 cm in length and 7 cm in diameter filled with 700 g. of Column-Lite and eluted with ethyl acetate-methanol mixture (1:1). Yellow fractions containing aclacinomycin A were evaporated to dryness in vacuo. 12.4 g. of crude aclacinomycin A was dissolved in 100 ml. of chloroform and added to 50 ml. of $10^{-3}M$ EDTA in 0.01 M phosphate buffer (pH 6.8). After shaking vigorously to remove residual metal ions, the chloroform phase was washed twice by shaking with water, dried over anhydrous sodium sulphate and evaporated to dryness in vacuo. 11.1 g. of aclacinomycin A was obtained as yellow powder.

"Sephadex LH-20" is a lypophilic insoluble molecular-sieve chromatographic medium made by cross-linking dextran and marketed by Pharmacia, Uppsala, Sweden. The Sephadex LH-20 used in the preceding examples can be replaced by other similar gel-filtration agents, e.g. Sephadex G25 to G200, Sepharose 4B and 6B (Pharmacia Fine Chemicals AB, Uppsala, Sweden) and Bio-Gel A1.5m (Bio Rad Co.). Preferred gel-filtration agents include the carboxymethyl substituted cross-linked dextran gels described in columns 3 and 4 of U.S. Pat. No. 3,819,836.

We claim:

1. A compound of the formula

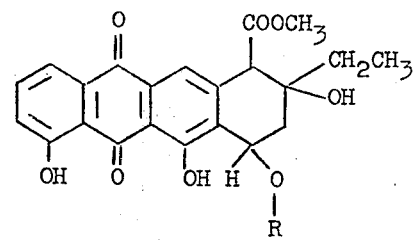

wherein R represents

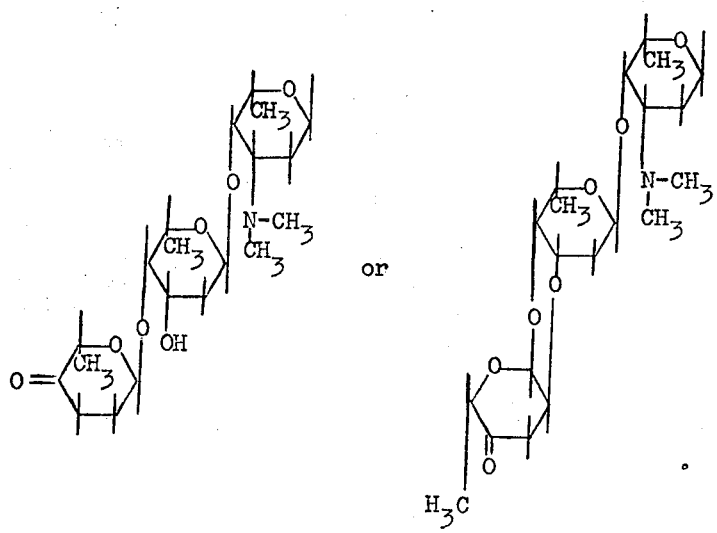

2. The compound of the formula
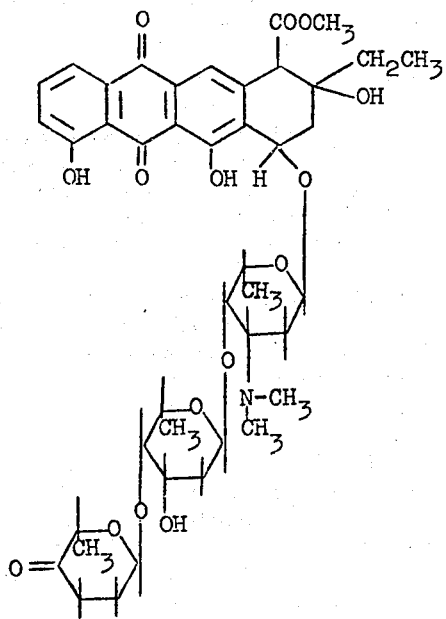
3. The compound of the formula
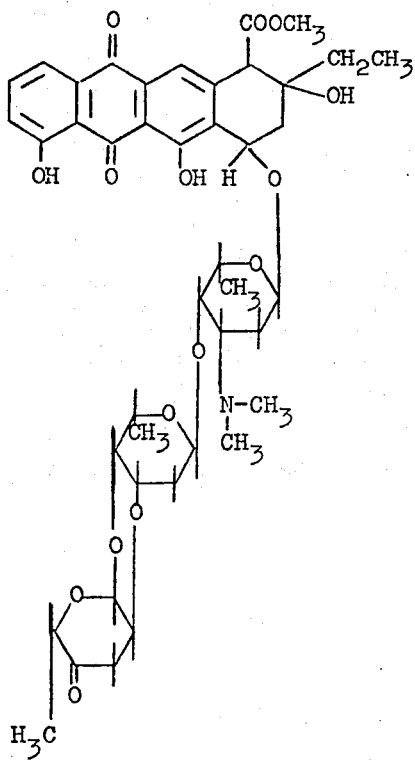
* * * * *